United States Patent [19]

Boehme

[11] 4,234,427

[45] Nov. 18, 1980

[54] PULSE DAMPER

[75] Inventor: Detlef R. Boehme, Walnut Creek, Calif.

[73] Assignee: Varian Associates, Inc., Palo Alto, Calif.

[21] Appl. No.: 45,033

[22] Filed: Jun. 4, 1979

Related U.S. Application Data

[63] Continuation-in-part of Ser. No. 911,853, Jun. 2, 1978, abandoned.

[51] Int. Cl.³ ............................................. B01D 15/08
[52] U.S. Cl. ................................ 210/198 C; 210/349; 138/30; 417/540
[58] Field of Search ........................... 210/198 C, 349; 417/540–543; 138/30

[56] References Cited

U.S. PATENT DOCUMENTS

| | | | |
|---|---|---|---|
| 3,013,696 | 12/1961 | Tralmer | 417/540 X |
| 3,537,585 | 11/1970 | Waters | 210/349 X |
| 3,766,992 | 10/1973 | Tiraspolsky | 417/540 X |
| 3,874,417 | 4/1975 | Clay | 417/540 X |
| 4,024,061 | 5/1977 | Gatiss | 210/349 |

OTHER PUBLICATIONS

Industrial Instruments for Measurement and Control by Rhodes, p. 34, McGraw-Hill Book Co., N.Y., N.Y., 1941.

*Primary Examiner*—John Adee
*Attorney, Agent, or Firm*—Stanley Z. Cole; Peter J. Sgarbossa; Keiichi Nishimura

[57] ABSTRACT

A pulse damper for use in high-pressure liquid pumping applications such as liquid chromatography comprises a length of flattened polytetrafluoroethylene tubing that can be coupled to the high-pressure liquid flow line. The flattened tubing is enclosed within a liquid-tight housing structure completely filled with a compressible liquid, and the end of the tubing are coupled to the high-pressure flow line by fittings mounted inside the housing structure. When a transient pressure variation occurs in the flow line, the cross-section of the tubing changes from a flattened elliptical configuration to a more rounded configuration as the pressure pulse temporarily overcomes the stresses that tend to maintain the tubing in its flattened configuration. The restoring force of the compressible liquid in the housing structure surrounding the tubing prevents expansion of the tubing beyond a desired limit during a pulse, so that the tubing cannot burst when its cross-sectional configuration changes. The overall length of the tubing, related to the volume and compressibility of the compressible liquid, the highest anticipated pulse pressure in the flow line, and the pre-determined maximum change to be allowed in the average cross-sectional area of the tubing, is generally much greater than the length of the housing structure, and hence the tubing is folded or coiled within the housing structure. Dissipation of the transient energy of a pulse in compressing the liquid in the housing structure effectively damps the pulse.

16 Claims, 3 Drawing Figures

PULSE DAMPER

DESCRIPTION

This is a continuation-in-part application Ser. No. 911,853 filed June 2, 1978, now abandoned.

BACKGROUND OF THE INVENTION

This invention relates generally to the damping of pulsations in a high-pressure flow line of a liquid pumping system.

A particular application of this invention is in a high-pressure liquid chromatography system in which a carrier liquid containing a quantity of a sample to be analyzed is delivered to a chromatographic column in pulses by the action of a reciprocating pump. In order to provide a continuous flow of liquid to the chromatographic column, it is necessary to insert a pulse damper in the flow line between the reciprocating pump and the chromatographic column.

In one pulse damping technique used in a prior liquid chromatography invention, a block of plastic material (typically, polytetrafluoroethylene) was placed in the flow line between the reciprocating pump and the chromatographic column. The plastic block stored energy by compressing during that portion of the pumping cycle when the pressure in the flowline was increasing, and subsequently released the stored energy by decompressing as the pressure in the flow line was decreasing, whereby pressure pulses in the outflow from the reciprocating pump over a full pumping cycle were damped. A pulse damper of this kind is described in U.S. Pat. No. 4,024,061.

With such pulse damping devices in which a compressible body was disposed directly in the flowline, the damping characteristics of the compressible body could not generally be matched with the pulsing characteristics of the pump. Although different materials have different compressibility characteristics, the choice of materials for the body to be disposed directly in liquid chromatography flow line was limited to those plastics that are chemically inert with respect to the kinds of solvents used in liquid chromatography. Only a few plastic materials, such as polytetrafluoroethylene (Teflon), and polychlorotrifluoroethylene (Kel-F), can meet this requirement. Thus, the damping characteristics of a pulse damper of this type could not generally be selected on the basis of the pulsing characteristics of the pump.

Furthermore, with prior pulse dampers utilizing a compressible body disposed in the high-pressure flowline, the obstruction of the flow line by the compressible body tended to cause non-laminar flow and turbulence that resulted in cavitations. In chromatographic applications, such cavitations tend to interfere with the analysis of the flow line constitutents. In general, for chromatographic applications, a smooth flow path for the flowline liquid through the pulse damper is to be preferred, because discontinuities in the flow path tend to create "dead volumes" within which minute quantities of the flow line liquid could become trapped. Such trapped quantities of flow line liquid are a source of contamination for chromatograhic analysis systems.

Another pulse damping technique used previously involved passing the flowing liquid into a first chamber that is separated from a larger second chamber by a flexible diaphragm. The larger second chamber is filled with a compressible liquid. For a uniform flow rate through the first chamber, the diaphragm maintains a quiescent configuration in separating the first and second chambers. However, when a pulse occurs in the flowline liquid passing through the first chamber, the diaphragm flexes towards the second chamber, thereby temporarily compressing the liquid in the second chamber for the duration of the pulse. The work done by the energy of the pulse in compressing the liquid in the second chamber effectively damps the pulse. At the end of the pulse, the restoring force of the compressed liquid in the second chamber causes the diaphragm to return to its quiescent configuration.

SUMMARY OF THE INVENTION

It is an object of the present invention to provide a novel pulse damper for a high-pressure liquid pumping system, whereby pressure transients in high-pressure liquid flow line can be dissipated in compressing an enclosed liquid surrounding the flow line. A pulse damper according to the present invention comprises a flattened tubular member having an input end and an output end, and housed within a structure containing a compressible liquid. The tubular member is coupled to the high-pressure liquid flow line, and is pre-flattened to maintain a generally elliptical cross-sectional configuration in the absence of pulsations in the flow line. When a pressure pulse occurs in the flow line, the cross-sectional configuration of the tubular member becomes rounded.

It is a more specific object of this invention to provide a pulse damper for use in a liquid chromatography system. A pulse damper according to this invention permits a substantially unobstructed flow of high-pressure fluid from a reciprocating pump to a chromatographic column. The pulse damper comprises a flexible tubular member that assumes a first configuration in the absence of a pressure pulse in the flowline and a second configuration when a pressure pulse is present in the flowline. The tubular member is completely surrounded by an enclosed compressible liquid, which limits the expansion of the tubular member during a pulse. In this way, a pressure pulse in the flow line can be dissipated in compressing the surrounding liquid while the tubular member changes from the first to the second configuration.

It is an object of the present invention to provide a means for damping pulsations in the flow line of a high-pressure liquid pumping system, where the pulse damping means comprises a flexible tubular member coupled to the pumping system flow line. The tubular member is pre-formed to maintain a generally flattened configuration in the absence of a pulse in the flow line. When a pulse occurs in the flow line, the stresses that tend to maintain the flattened configuration are overcome and the tubular member assumes a more-or-less rounded configuration without, however, expanding circumferentially. The final cross-sectional configuration depends upon the magnitude of the pulse. A pulse of sufficient magnitude would change the cross-sectional shape of the tubular member all the way from a flattened configuration to a fully rounded configuration. A pulse of lesser magnitude would cause the cross-sectional shape of the tubular member to change to an oval configuration. The tubular member is enclosed within a liquid-field housing structure, whereby a pulse in the tubular member would compress the surrounding liquid. The restoring force exerted by the compressed surrounding liquid prevents radial expansion of the tubular member beyond the desired limit, and makes certain that there is substantially no circumferential expansion so that the tubular member cannot burst when changing its cross-sectional configuration in response to a pulse in the flow line. In this way, the energy carried by a pulse can be stored temporarily in the compressed liquid for the duration of the pulse thereby damping the pulsations in the flow line.

It is a particular object of this invention to provide a means for damping pulsations in the flow line of a high-pressure liquid chromatography system in which a reciprocating pump delivers a carrier liquid through a flow line to an injector device where sample material can be injected and "carried" to a chromatographic column for analysis. It is a feature of this invention that the pulse damping means comprises a tubular member coupled to the high-pressure flow line. The tubular member is preflattened to maintain a generally elliptical cross-section configuration in the absence of pulses therein. When a pulse occurs, the cross-section of the tubular member becomes rounded. The tubular member is enclosed within a liquid-tight housing structure, and the interior of the housing structure is completely filled with a compressible liquid such as isopropyl alcohol or silicone oil. The coupling of the tubular member to the high-pressure flow line is accomplished by fittings disposed within the housing structure. Energy carried by a pulse in the flow line liquid passing through the tubular member is temporarily stored for the duration of the pulse by the compressible liquid in the housing structure surrounding the tubular member as the tubular member changes shape in response to the pulse. At the end of the pulse, both the compressed liquid and the tubular member respond rapidly as the restorative force quickly releases the stored energy back to the flow line liquid, and the tubular member returns to its flattened cross-sectional configuration while at the same time the tubular member is flushed efficiently because there are no dead volumes in the flow passage. In this way, pulsations in the flow-line liquid are damped so that a substantially steady flow can be delivered to the chromatographic column.

In a preferred embodiment of this invention, a tubular member made of a plastic material that is chemically compatible with the liquid being pumped through a high-pressure flow line is disposed within a generally cylindrical housing structure. It is preferably continuous, of one-piece construction and of substantially uniform circumference throughout so that the original flattened configuration is rapidly restored and the tube is efficiently flushed immediately after the end of a pressure pulse. In liquid chromatographic applications, the tubular member may be made of polytetrafluoroethylene (marketed under the Teflon brand name), which is chemically inert with respect to the solvents generally used in liquid chromatography. Where greater mechanical flexibility is required than can be provided by polytetrafluoroethylene, the tubular member could be made of perfluoroelastomer (a material marketed under the Kalrez brand name). The housing structure may be made of stainless steel, and is provided with a threaded end cap on each end. Suitable fittings projecting into the interior of the housing structure are maintained in place by the end caps to provide means for connecting the tubular member to the high-pressure flow line. The interior walls of the housing structure define a liquid-tight cavity which completely envelopes the tubular member, both ends of which terminate at the walls of the housing structure. This liquid-tight cavity bounded by the inner walls of the housing structure and the tubular member is completely filled with a compressible liquid such as isopropyl alcohol or silicone oil so that an increase in the cross-sectional area of the tubular member immediately compresses this enclosed liquid. The length of the tubular member is determined so that the compressible liquid in the liquid-tight cavity can be compressed to a sufficient degree so as to prevent the radial expansion of the tubular member from exceeding a predetermined level. The flow line liquid flowing through the tubular member is isolated from the compressible liquid in the housing structure by appropriate compression fittings.

The tubular pulse damping member of the preferred embodiment is pre-flattened to assume a generally elliptical cross-sectional shape in the absence of pulsations in the flow-line fluid. For a flexible material such as polytetrafluoroethylene, this flattened configuration is relatively unstable with respect to internal pressure pulses, and is therefore readily changed to a more rounded configuration even by pulses of small magnitude. When a pressure pulse occurs in the flow line, the liquid surrounding the flattened tubular member is compressed as the tubular member assumes a more rounded cross-sectional configuration. Thus, the energy of the pulse is temporarily stored in the surrounding liquid for the duration of the pulse, and a pulse damper according to the present invention provides rapid response to pressure transients in a high-pressure liquid flow line. A substantially smooth flow of the flow-line fluid is thereby provided.

DESCRIPTION OF THE PREFERRED EMBODIMENTS

Figure 1:
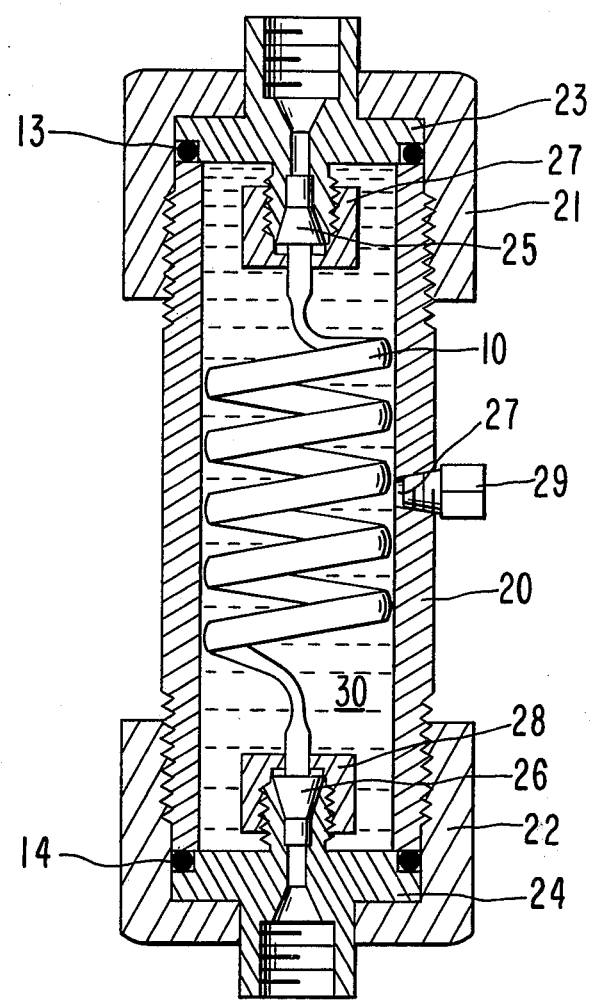
FIG. 1 shows a cross-sectional view of the pulse damper according to the present invention, in which a flattened flexible tubular member is coiled transversely within a cylindrical housing structure.

In FIG. 1, a cross-sectional view of a pulsation damper according to the present invention is shown. A flattened tubular member 10 made out of a flexible plastic material such as polytetrafluoroethylene is disposed within a generally cylindrical housing structure 20 made of stainless steel. The ends of the housing structure 20 are threaded, and are covered with matingly threaded end caps 21 and 22, respectively, which may likewise be made of stainless steel. The end caps 21 and 22 serve to retain coupling structures 23 and 24, respectively, at either end of the housing structure 20, whereby the tubular member 10 can be connected at each end to a high-pressure liquid flow line in which transient variations in pressure can occur.

The coupling structures 23 and 24 have smooth axial bores to accommodate unobstructed passage of flow-line liquid into, through, and out of the tubular member 10. Threaded projecting portions of the coupling structures 23 and 24 extend axially into the interior of the cylindrical housing structure 20, whereby the ends of the tubular member 10 can be connected to the coupling structures 23 and 24, respectively, inside the housing structure 20.

The ends of the tubular member 10 are inserted into deformable ferrules 25 and 26, respectively. Ferrule 25 fits snugly into the conformably configured bore of coupling structure 23, and ferrule 26 fits snugly into the conformably configured bore of coupling structure 24. Nuts 27 and 28, when tightened around the threaded projecting portions of the coupling structures 23 and 24, respectively, compress the ferrules 25 and 26.

Figure 3:
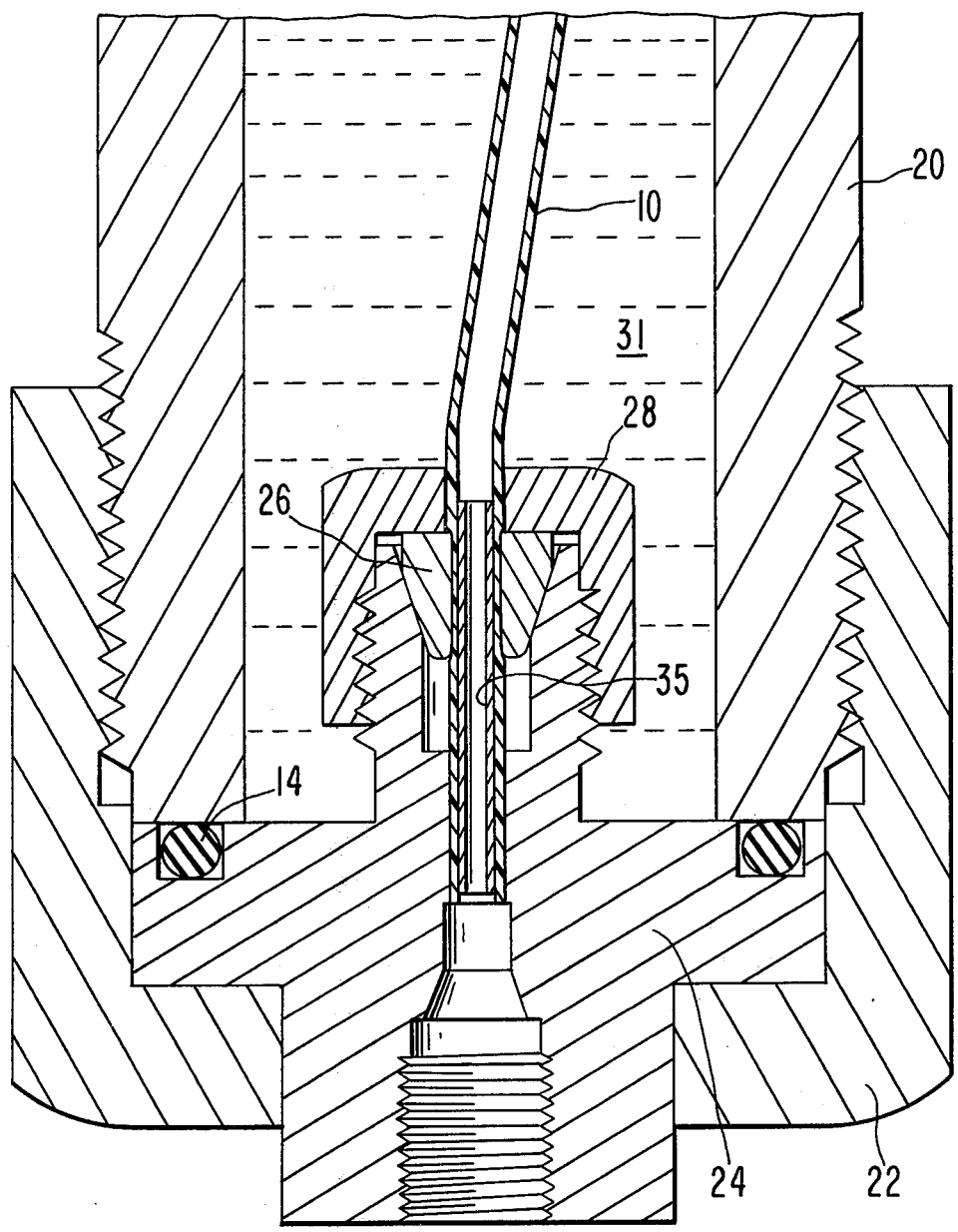
FIG. 3 is a fragmentary cross-sectional view of the pulse damper, showing the details of the compression fitting encompassed within curved section line 3—3 of FIG. 2.

The mechanism for liquid-tight connection between the tubular member 10 to the bores of the coupling structures 23 and 24 is shown in detail in FIG. 3. A straight cylindrical pipe 35, preferably made of stainless steel, is fitted inside the tubular member 10 in the region where the tubular member 10 passes through the nut 28 and the deformable ferrule 26. The nut 28, when tightened so as to compress the ferrule 26 against the conformably configured bore of the coupling structure 24, also presses the ferrule 26 radially inward to compress the walls of the flexible tubular member 10 against the cylindrical pipe 35 fitted therein. In this way, a liquid-tight seal is provided, connecting the flexible tubular member 10 to the bore of the coupling structure 24. Connection of the coupling structures 23 and 24 to the high-pressure liquid flow line externally of the housing structure 20 is provided by conventional means well known to those skilled in the high-pressure liquid chromatography art. The tubular member 10, when thus connected to the flow line, becomes in effect a part of the flow line because the flow line liquid passes therethrough.

FIG. 1 further shows a sealable port 30 which is provided in the housing strucutre 20, whereby the interior cavity 31 thereof can be completely filled with a compressible liquid such as isopropyl alcohol or silicone oil. The port 30 is sealed by a plug 29. Liquid-tight seals between the coupling structures 23 and 24 and the housing structure 20 are provided by O-rings 13 and 14 disposed at respective ends thereof. Tightening of the end cap 21 over the coupling structure 23 compresses the O-ring 13 so as to provide a liquid-tight seal between the coupling structure 23 and one end of the housing structure 20, and tightening of the end cap 22 over the coupling structure 24 compresses the O-ring 14 so as to provide a liquid-tight seal between the coupling structure 24 and the other end of the housing structure 20.

The flexible tubular member 10 is pre-formed to have a generally elliptical (i.e., flattened) cross-sectional configuration, except at its ends where it is connected to the coupling structures 23 and 24. Its total length L is so determined as to satisfy the requirement that substantially all of the pulsation energy be temporarily absorbed by the surrounding liquid.

This may be determined from a somewhat simplified relationship between the volume of liquid in housing 20, its compressibility, the pressure of the pulse in member 10, and the change in volume displaced by member 10 under the influence of the pulse. For simplicity, this treatment assumes steady state conditions, but in reality, the pulses arrive at the damper at high repetitive rates, and the damper operation is at correspondingly very rapid rates. Let the volume and compressibility of the compressed liquid in housing 20 be V and X, respectively. Let the maximum anticipated change in pressure in the flow line be dp. Such change in pressure, when entirely applied to the liquid, will cause its volume to change by $dV = V \times dp$. Since the compressible liquid completely fills the cavity inside the liquid-tight housing 20, dV must be equal to the increase in volume of tubular member 10, or the additional differential displacement volume of member 10 in the liquid when a high pressure pulse causing pressure change dp passes therethrough, as compared to its displacement volume when the tube is in its flattened state, with no pulse present. As the tube increases in volume under the influence of the high pressure pulse, the tube changes from its flattened cross-sectional configuration to its rounded cross-sectional configuration, with the cross-sectional area in the rounded configuration, of course, being larger than that of the flattened configuration. If L is the length of tubular member 10, and dA is the additional differential cross-sectional area corresponding to the pressure increase dp due to a pulse, then LdA represents the overall increase in volume of tubular member 10. Thus, $dV = LdA = V \times dp$.

Then if the maximum change in pressure due to a pulse, the volume of liquid, and its compressibility are known, the volume change in the liquid is determinable. The maximum differential cross-sectional area dA, or the increase in the average cross-sectional area, is predetermined due to the requirement that substantially no circumferential expansion of tubular member 10 is desired, to preclude stressing or distending the walls thereof, the consequent fatiguing thereof, and eventual bursting of the member. Accordingly, the length L of tubular member necessary under these conditions can then be determined. In this manner, the energy of the high pressure pulse is stored primarily as a compressive force in the liquid, a balance is achieved between the pressure exerted by the pulse and the restorative force of the compressed liquid, and the tubular member's change in cross-sectional area is limited to a size which does not stretch or distend the circumference of the member.

Of course, once the high pressure ceases, the substantial force of the compressed liquid in housing 20 immediately acts upon tubular member 10 to restore the tube to its flattened configuration, and in so doing, thoroughly flushes tubular member 10, thereby minimizing cross-sample contamination. Furthermore, the substantial storage of pulse pressure in the compressed liquid gives rise to a very rapid and almost immediate restorative action, enabling the pulse damper to handle incoming pulses at extremely high repetitive rates.

The length L, as determined above, is generally quite large. As shown in FIG. 1, the tubular member 10 is coiled transversely within the cylindrical housing structure 20 into a generally helical configuration in order to permit a length of tubing that is many times greater than the length of the housing structure 20 to be fitted into the housing structure 20. (For a housing structure of 5-inch length, the overall length of the tubular member 10 could advantageously be on the order of 27 inches.) In this way, the ratio of the interior volume of the tubular member 10 to the volume of the compressible liquid in the cavity 30 is such as to permit dissipation of the energy in a pressure pulse in the tubular member 10 by compressing the liquid in the cavity 30 without causing radial expansion of the tubular member 10 beyond a desired limit. Thus, bursting of the tubular member 10 can be prevented at the highest anticipated operating pressure for the flow line.

Figure 2:
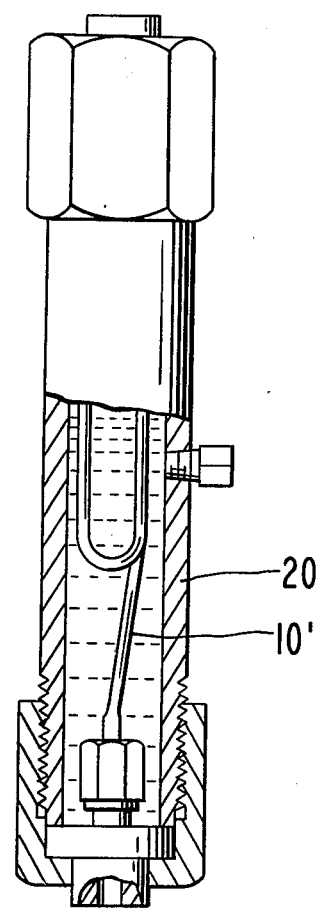
FIG. 2 shows a cross-sectional view of an alternative embodiment of a pulse damper according to the present invention, in which a flattened flexible tubular member is folded longitudinally within a cylindrical housing structure.

In the alternative embodiment shown in FIG. 2, the flexible tubular member 10' is folded longitudinally within the cylindrical housing structure 20, rather than being coiled transversely as shown in FIG. 1.

This invention has been described above in terms of particular embodiments. The above description, however, is to be considered as illustrative rather than as limiting. The scope of the invention is defined by the following claims.

I claim:

1. In a liquid chromatography system comprising a reciprocating pump, a chromatographic column, a flow line connecting said pump to said column for delivering fluid from said pump to said column, and a pulse damper coupled into said flow line for damping high pressure pulsations in said flow line, said pulse damper comprising:
   a flexible tubular member in series with said flow line;
   a liquid-tight housing structure surrounding said tubular member, said structure being completely filled with a compressible liquid;
   said tubular member having a first flattened non-circular cross-sectional configuration in the absencr of said pulsations, said member being capable, upon occurrence of a high pressure pulsation, of assuming a second cross-sectional configuration of area greater than said first configuration of area greater than said first configuration, with the circumference of said tubular member experiencing minimal expansion;
   said tubular member in said second cross-sectional configuration displacing an additional differential displacement volume dV as compared to the original volume displaced by said member in said first configuration;
   the volume V and compressibility X of said compressible liquid being related to said differential volume dV such that dV/XV is greater than the highest anticipated pressure change in said flow line;
   whereby said tubular member accommodates high pressure fluid pulsations without risk of bursting, sustaining only minimal circumferential expansion, and whereby the energy of said high pressure pulses is stored primarily as a compressive force in said liquid, to effect said damping.

2. The liquid chromatography system of claim 1 wherein said pulse damper further comprises means for coupling said tubular member to said flow line, said coupling means comprising a coupling structure at each end of said housing structure, each coupling structure having a portion projecting into said housing structure, said projecting portion having a bore therethrough to permit passage of flow line liquid through said coupling structure, each end of said tubular member being connected within said housing structure to said projecting portion of a respective one of said coupling structure.

3. The liquid chromatography system of claim 2 wherein said coupling means further comprises a hollow cylindrical pipe tightly fitting inside said tubular member and a deformable ferrule through which said tubular member passes, whereby pressure applied on said ferrule in the axial direction compresses said tubular member radially inward against the outer walls of said cylindrical pipe.

4. The liquid chromatography system of claim 3 wherein said deformable ferrule fits snugly into said bore and said coupling means further comprises means for compressing said ferrule axially against said bore.

5. The liquid chromatography system of claim 4 wherein the end of said projecting portion of said coupling structure is threaded and said compressing means comprises a nut fitting into said projecting portion, whereby said nut, when tightened, compresses said ferrule against said bore.

6. The liquid chromatography system of claim 1 wherein said flexible tubular member comprises a plastic tube, at least a portion of said tube being pre-formed to maintain a generally elliptical cross-sectional configuration in the absence of a pulse in said flow line.

7. The liquid chromatography system of claim 1 wherein said flexible tubular member is made of polytetrafluoroethylene.

8. The liquid chromatography system of claim 1 wherein said flexible tubular member is made of perfluoroelastomer.

9. The liquid chromatography system of claim 1 wherein the length of said tubular member is greater than the length of said housing structure.

10. The liquid chromatography system of claim 9 wherein said tubular member is folded longitudinally within said housing structure.

11. The liquid chromatography system of claim 9 wherein said tubular member is coiled within said housing structure.

12. The liquid chromatography system of claim 1, wherein said second cross-sectional configuraion is circular.

13. The liquid chromatography system of claim 1 wherein said second tubular member upon assuming said cross-sectional configuration upon said occurrence of said high pressure pulsation, experiences substantially no change in circumference.

14. The liquid chromatography system of claim 1 wherein said compressible liquid is isopropyl alcohol.

15. The liquid chromatography system of claim 1 wherein said compressible liquid is silicone oil.

16. An apparatus for damping high pressure pulsations in a liquid flow line, comprising:
    a deformable tubular member having an input end and an output end;
    a housing having walls defining a liquid-tight cavity which envelopes said member, said input and output ends thereof terminating at said walls of said housing;
    input and output connector means mounted within said housing walls and respectively connecting said input and output ends of said tubular member in series with said flow line;
    a compressible liquid completely filling the volume of said cavity not occupied by said tubular member;
    said member having a first flattened configuration in the absence of one of said high pressure pulsations, said member being capable of assuming a second larger, circular cross-sectional configuration wherein the walls of said tube remain substantially undistended;
    the length L and average differential cross-sectional area dA of said sube being so related to the volume V and compressibility X of said liquid as to make LdA/XV larger than the highest anticipated pressure change in said flow line, whereby said tubular member displaces, additional volume upon occurrence of a high pressure pulsation, said liquid is compressed only to the extent of the displaced volume due to said second tubular member configuration at the highest expected operating pressure, thereby preventing the risk of tube expansion beyond said second configuration and consequent bursting, the energy of the pulse is stored substantially as a compressive force in said liquid, and said compressed liquid responds rapidly to restore said tubular member to said first flattened configuration and to flush said tubular member immediately thereafter.

* * * * *